(12) United States Patent
Weber

(10) Patent No.: US 7,037,319 B2
(45) Date of Patent: May 2, 2006

(54) NANOTUBE PAPER-BASED MEDICAL DEVICE

(75) Inventor: Jan Weber, Maple Grove, MN (US)

(73) Assignee: Scimed Life Systems, Inc., Maple Grove, MN (US)

( * ) Notice: Subject to any disclaimer, the term of this patent is extended or adjusted under 35 U.S.C. 154(b) by 548 days.

(21) Appl. No.: 10/270,815

(22) Filed: Oct. 15, 2002

(65) Prior Publication Data

US 2004/0073251 A1    Apr. 15, 2004

(51) Int. Cl.
*A61M 29/00*    (2006.01)

(52) U.S. Cl. .................................... 606/192

(58) Field of Classification Search ............... 606/108, 606/191–198; 623/1.1, 1.11
See application file for complete search history.

(56) References Cited

U.S. PATENT DOCUMENTS

| | | |
|---|---|---|
| 4,273,128 A | 6/1981 | Lary |
| 4,765,332 A | 8/1988 | Fischell et al. |
| 4,926,858 A | 5/1990 | Gifford, III et al. |
| 4,954,388 A | 9/1990 | Mallouk et al. |
| 4,963,313 A | 10/1990 | Noddin et al. |
| 4,979,951 A | 12/1990 | Simpson |
| 5,047,040 A | 9/1991 | Simpson et al. |
| 5,049,131 A | 9/1991 | Deuss |
| 5,092,872 A | 3/1992 | Segalowitz |
| 5,209,728 A | 5/1993 | Kraus et al. |
| 5,234,450 A | 8/1993 | Segalowitz |
| 5,300,203 A | 4/1994 | Smalley |
| 5,320,634 A | 6/1994 | Vigil et al. |
| 5,336,234 A | 8/1994 | Vigil et al. |
| 5,397,308 A | 3/1995 | Ellis et al. |
| 5,401,587 A | 3/1995 | Motohiro et al. |
| 5,415,634 A | 5/1995 | Glynn et al. |
| 5,424,054 A | 6/1995 | Bethune et al. |
| 5,442,286 A * | 8/1995 | Sutton et al. ............... 324/242 |
| 5,490,837 A | 2/1996 | Blaeser et al. |
| 5,538,585 A | 7/1996 | Wakita et al. |
| 5,543,378 A | 8/1996 | Wang |
| 5,549,807 A | 8/1996 | Bell et al. |
| 5,591,312 A | 1/1997 | Smalley |
| 5,616,149 A | 4/1997 | Barath |
| 5,645,564 A | 7/1997 | Northrup et al. |
| 5,715,832 A | 2/1998 | Koblish et al. |
| 5,792,158 A | 8/1998 | Lary |
| 5,853,886 A | 12/1998 | Pinnavaia et al. |
| 5,873,907 A | 2/1999 | Frantzen |
| 5,916,642 A | 6/1999 | Chang |
| 5,919,145 A | 7/1999 | Sahatjian |
| 6,019,656 A | 2/2000 | Park et al. |

(Continued)

FOREIGN PATENT DOCUMENTS

WO    WO 93/11190    6/1993

(Continued)

OTHER PUBLICATIONS

International Search Report for PCT/US03/31482 mailed Jul. 16, 2004.

(Continued)

*Primary Examiner*—Kevin T. Truong

(57) ABSTRACT

A medical device is disclosed which may include the use of carbon nanotube paper. The medical device may be provided in the form of a balloon catheter wherein the nanotube paper is mounted about an electrode and into which an electrically conductive fluid is dispersed. An elastomeric sheath may then be provided about the nanotube paper. Actuation of the electrode may cause generation of microbubbles within the fluid and thereby cause the paper to expand.

8 Claims, 3 Drawing Sheets

U.S. PATENT DOCUMENTS

| | | | |
|---|---|---|---|
| 6,042,959 | A | 3/2000 | Debe et al. |
| 6,056,720 | A | 5/2000 | Morse |
| 6,074,773 | A | 6/2000 | Wilkinson et al. |
| 6,080,170 | A | 6/2000 | Nash et al. |
| 6,090,135 | A | 7/2000 | Plaia et al. |
| 6,096,054 | A | 8/2000 | Wyzgala et al. |
| 6,110,192 | A | 8/2000 | Ravenscroft et al. |
| 6,135,991 | A | 10/2000 | Muni et al. |
| 6,136,258 | A | 10/2000 | Wang et al. |
| 6,149,775 | A | 11/2000 | Tsuboi et al. |
| 6,152,938 | A | 11/2000 | Curry et al. |
| 6,183,714 | B1 | 2/2001 | Smalley et al. |
| 6,258,108 | B1 | 7/2001 | Lary |
| 6,302,906 | B1 | 10/2001 | Goicoechea et al. |
| 6,319,242 | B1 | 11/2001 | Patterson et al. |
| 6,346,023 | B1 | 2/2002 | Tsuboi et al. |
| 6,387,560 | B1 | 5/2002 | Yadav et al. |
| 6,425,908 | B1 | 7/2002 | Ravenscroft et al. |
| 6,425,914 | B1 | 7/2002 | Wallace et al. |
| 6,447,478 | B1 | 9/2002 | Maynard |
| 6,458,128 | B1 | 10/2002 | Schulze |
| 6,468,266 | B1 | 10/2002 | Bashiri et al. |
| 6,530,948 | B1 | 3/2003 | Vrba |
| 6,538,262 | B1* | 3/2003 | Crespi et al. ............... 257/40 |
| 6,545,384 | B1 | 4/2003 | Pelrine et al. |
| 6,555,945 | B1 | 4/2003 | Baughman et al. |
| 6,576,365 | B1 | 6/2003 | Meitav et al. |
| 6,585,753 | B1 | 7/2003 | Eder et al. |
| 6,589,682 | B1 | 7/2003 | Fleckner et al. |
| 6,592,568 | B1 | 7/2003 | Campbell |
| 6,607,551 | B1 | 8/2003 | Sullivan et al. |
| 6,626,934 | B1 | 9/2003 | Blaeser et al. |
| 2002/0062122 | A1 | 5/2002 | Lehmann et al. |
| 2002/0068170 | A1 | 6/2002 | Smalley et al. |
| 2002/0122766 | A1 | 9/2002 | Lieber et al. |
| 2002/0179434 | A1 | 12/2002 | Dai et al. |
| 2003/0032892 | A1 | 2/2003 | Erlach et al. |
| 2003/0055407 | A1 | 3/2003 | Walik |
| 2003/0065355 | A1 | 4/2003 | Weber |
| 2003/0068432 | A1 | 4/2003 | Dai et al. |
| 2003/0093107 | A1 | 5/2003 | Parsonage et al. |
| 2003/0133865 | A1 | 7/2003 | Smalley et al. |
| 2003/0135971 | A1 | 7/2003 | Liberman et al. |
| 2003/0143350 | A1 | 7/2003 | Jimenez |
| 2003/0171257 | A1 | 9/2003 | Stirbl et al. |
| 2003/0180472 | A1 | 9/2003 | Zhou et al. |
| 2003/0185985 | A1 | 10/2003 | Bronikowski et al. |

FOREIGN PATENT DOCUMENTS

| | | |
|---|---|---|
| WO | WO 01/34685 | 5/2001 |
| WO | WO 02/082974 | 10/2002 |
| WO | WO-03/026532 A2 | 4/2003 |
| WO | WO-03/049795 A2 | 6/2003 |

OTHER PUBLICATIONS

Partial International Search Report PCT/US 03/31482; report dated Apr. 27, 2004.

"Use of Commercial Porous Ceramic Particles for Sustained Drug Delivery," Byrne et al., Int. J. Pharmaceutics, 246:61-73 (2002).

"Plasma Activation of Carbon Nanotubes for Chemical Modification," Chen et al., J. Phys. Chem., 105:618-622 (2001).

"Steerable Microcatheters Actuated by Embedded Conducting Polymer Science," Della Santa et al., J. Intell., Mater. Sys. Struct., 7:292-300 (1996).

"Chemical Functionalization of Single Walled Carbon Nanotubes," Dettlaff-Weglikowska et al., Curr. Appl. Phys., 2:497-507 (2002).

"Organic Functionalization of Carbon Nanotubes," Georgakilas et al., J. Am. Chem., 124:760-761 (2002).

"Special Delivery. Alternative Methods for Delivering Drugs Improve Performance, Convenience, and Patient Compliance," Henry et al., Science/Technology, 78:49-65 (2000).

"Supramolecular Structures of Novel Carbohydrate-Based Phospholipids," Hird et al., J. Am. Chem. Soc., 122:8097-8098 (2000).

"Chemical and Physiochemical Characterization of Porous Hydroxyapatite Ceramics Made of Natural Bone," Joschek et al., Biomaterials, 21:1645-1658 (2000).

"Ion-Irradiation-Induced Welding of Carbon Nanotubes," Krasheninnikov et al., Phys. Rev., 66:245403-1-245403-6.

"Fullerene Pipes," Liu et al., Science, 280:1253-1256 (1998).

"Carbon Nanotube Bucky Paper Scaffold for Retinal Cell Transplantation," Loftus, D., NASA (2003).

"PVDF-Based Proton Conducting Membranes as Electrolytes for Polymer Fuel Cells," Magistris et al., XXI Congresso Nazionale Della Societa' Chimica Italiana, (2003).

"Structures of High-Stage Donor-Acceptor Hetero-Structure Graphite Intercalation Compounds," Murakami et al., J. Phys. Soc. Japan, 59:571-578 (1990).

"The Expansion of the Carbon-Carbon Bond Length in Potassium Graphites," Nixon et al., J. Phys. C., 2:1732-1741 (1969).

"Synthesis, Structural Characterization, and Immunological Properties of Carbon Nanotubes Functionalized with Peptides," Pantarotto et al., J. Am. Chem., 125:6160-6164 (2003).

"Studies on the Drug Release Properties of Polysaccharide Multilayers Encapsulated Ibuprofen Microparticles," Qiu et al., Langmuir, 17:5375-5380 (2001).

"Elastic and Shear Moduli of Single-Walled Carbon Nanotube Ropes," Salvetat et al., Phys. Rev. Lett., 82:944-947 (1999).

"Electrochemical Muscles: Micromachining Fingers and Corkscrews," Smela et al., Adv. Mater., 5:630-632 (1993).

"Single-Wall Carbon Nanotube Films," Sreekumar et al., Chem. Mater., 15:175-178 (2003).

"Shape Memory Alloys: Functional and Smart," Stalmans et al., in Smart Materials and Technologies—Sensors, Control Systems and Regulators, Prague, Czech Republic, 1995.

"Gummy Drug Delivery," Stover, D., Popular Science, 2000.

"Mono-sized and Single Walled 4Å Carbon Nanotubes," Wang et al., Chem. Phys. Lett., 339:47-52(2001).

"Giant Electrostriction and Relaxor Ferroelectric Behavior in Electron-Irradiated Poly(vinylidene fluoride-trifluoroethylene) Copolymer," Zhang et al., Science, 280:2010-2104 (1998).

"Crystallization and Microstructure Analysis of Calcium Phosphate-Based Glass Ceramics for Biomedical Applications," Zhang et al., J. Non-Crystalline Solids, 272:14-21 (2000).

"Transport Properties of Triblock Copolymer Ionomer Membranes for Fuel Cells," U.S. Research Laboratory.

"Polymer Gel Holds Promise for Therapeutics Delivery and Tissue Engineering," EurekaAlert, www.eurekalert.org/pub_releases/2001-03/PNNL-Pghp-2803101.php.

"Alternative Formulations for the Anti-Cancer Drug Paclitaxel (Taxol)," Adriance-Meja et al., 2002.

"Sustained Release Properties of Polyelectrolyte Multilayer Capsules," Antipov et al., J. Phys. Chem., 105:2281-2284 (2001).

"Organic Solvent Dispersions of Single-Walled Carbon Nanotubes: Toward Solutions of Pristine Nanotubes," Ausman et al., J. Phys. Chem, 104:8911-8915 (2000).

"Functionalization of Carbon Nanotubes by Electrochemical Reduction of Aryl Diazonium Salts: A Bucky Paper Electrode," Bahr et al., J. Am. Chem. Soc., 123:6536-6542 (2001).

"Carbon Nanotubes—The Route Toward Applications," Baughman et al., 297:787-792 (2002).

"Carbon Nanotube Actuators," Baughman et al., Science, 284:1340-1644 (1999).

"Conducting Polymer Artificial Muscles," Baughman, R., Syn. Metals, 78:339-353 (1996).

"Albumin-Heparin Matrices Loaded with Growth Factor as Substrates for Endothelial Cell Seeding," Bos, G., Thesis, University of Twente, The Netherlands, 1968.

"Polymers in Controlled Drug Delivery," Brannon-Peppas, L., Medical Device Link, 1997.

"Smart Capsules," in *Multilayer Thin Films*, Chapter 13, 2003.

Electrochem Membrane Materials.

Foils List, Lebow Co.

Argonide Website.

Zyvex website.

GFD-Diamond website.

Macromed Website.

"Carbon Nanotubes as Actuators in Smart Structures," Monner et al., Proceedings of the SPIE—The International Society for Optical Engineering, vol. 5053, pp. 138-146.

"Carbon Nanotube/Polyelectrolyte Composites as Novel Actuator Materials," Chattopadhyay et al., Nanotubes and Related Materials, Symposium (Mater. Res. Soc. Symposium Proceedings, vol. 6363, p. A13.39, 1-6 (2001).

"Single Wall Carbon Nanotube—Nafion Composite Actuators," Landi et al., Nano Letters, vol. 2, No. 11, pp. 1329-1332, American Chem. Soc. (Nov. 2002).

"Practical Considerations for the Demonstration of Single Walled Carbon Nanotube Actuator," Minett et al., AIP Conference Proceedings Conference, AIP Cof. Proc. (USA), No. 591, pp. 585-589 (2001).

"Work Functions of Pristine and Alkali-Metal Intercalated Carbon Nanotubes and Bundles," Jijun et al., Physical Review B (Condensed Matter and Materials Physics), vol. 65, No. 19, pp. 193401/1-4 (May 15, 2002).

"The Effect of Solvent on Electrical Transport Properties in Single-Wall Carbon Nanotubes," Masubuchi et al., AIP Conference Proceedings Conference, AIP Conf. Proc. (USA), No. 590, pp. 233-236 (2001).

"Effect of Polymer and Solvent on Purification and Cutting of Single-Wall Carbon Nanotubes," Zhang et al., Chemical Physics Letters, vol. 349, No. 1-2, pp. 25-30 (Nov. 23, 2001).

"Pneumatic Carbon Nanotube Actuators," Spinks et al., Advanced Materials, vol. 14, No. 23, Dec. 3, 2002, pp. 1728-1732 (2002).

"Electrochemical Properties of Aligned Nanotube Arrays: Basis of New Electromechanical Actuators", Gao et al., Proceedings of the SPEI—The International Society for Optical Engineering, vol. 3987, pp. 18-24 (2000).

"Neutron-Diffraction Studies of $BaC_6$: c-Axis Compressibility, Carbon—Carbon Bond Length, and Charge Transfer," Fischer et al., Physical Review B, vol. 36, No. 8 (Sep. 15, 1987).

"Energetics and Structure of Single Walled Carbon Nanotoroids," Gao et al., California Institute of Technology, 11 pages (2002).

"Elastic Properties of Carbon Nanotubes and Nanoropes," Jian Ping Lu, Physical Review Letters, vol. 79: No. 7, 1297-1300 (1997).

"Single-wall carbon nanotubes," Paul L. McEuen, Physics World, 31-36 (2000).

"Carbon Nanotube (A big revolution in a technoloy that thinks very, very, very small)," Meyyappan et al., IEEE Potentials, 16-18 (2000).

"Large-scale purification of single-wall carbon nanotubes: process, product, and characterization," Rinzler et al., Appl. Phys. A 67, 29-37 (1998).

"Pneumatic Actuator Response from Carbon Nanotube Sheets," Spinks et al., Intellectual Polymer Research Institute, University of Wollongong, Mat. Res. Soc. Proc. vol. 706:8-13 (2002).

* cited by examiner

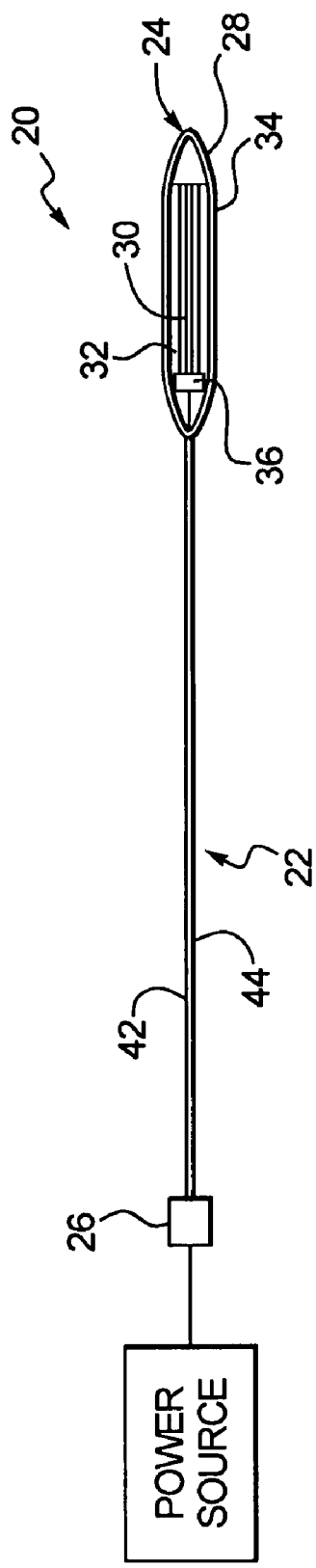
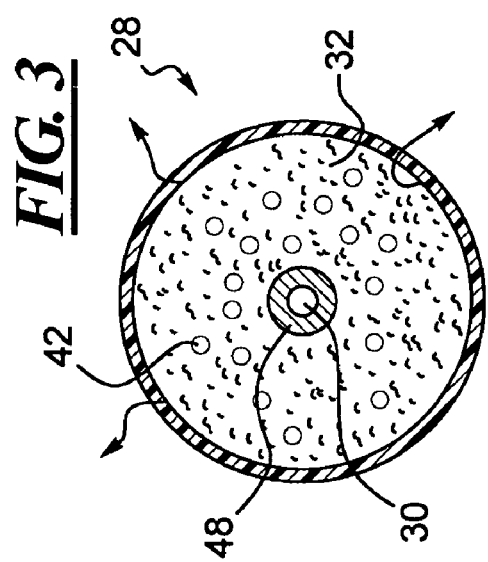
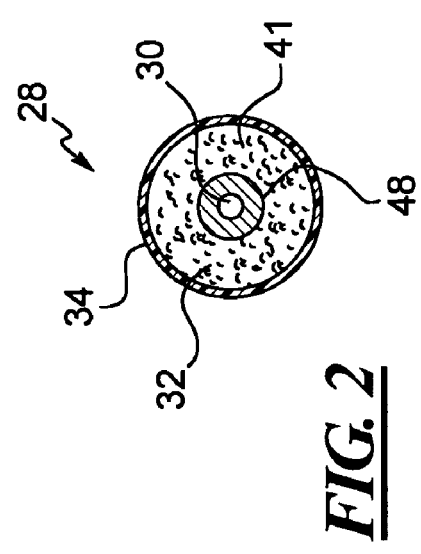

NANOTUBE PAPER-BASED MEDICAL DEVICE

FIELD OF THE DISCLOSURE

The present disclosure generally relates to medical devices and, more particularly, relates to catheters.

BACKGROUND OF THE DISCLOSURE

Angioplasty procedures are well known within the medical community. During such a procedure, a catheter is navigated through a lumen of the human body to a site needing expansion. For example, a distal portion of a catheter containing a deflated balloon is directed to an area of an artery which is substantially blocked, and which can be enlarged upon expansion of the balloon.

All currently known balloon catheters are pneumatically actuated. More specifically, the balloon catheter is manufactured from an elastomeric conduit with an enlarged diameter portion thereof forming a balloon. Upon the balloon reaching the procedure site, pressurized fluid is directed through the conduit and to the balloon so as to enlarge the diameter of the balloon, thereby imparting force against the interior walls of the lumen and thus expanding the blocked area. In order to minimize the entrance diameter of the puncture hole through the skin into the arterial system and thereby decrease the time for healing, as well as the amount of scar tissue after healing, it is of major importance to be able to reduce the diameter of the balloon catheter system while non-pressurized.

Currently such angioplasty catheters are being made using either compliant or non-compliant elastomeric material. Due to the necessity of being able to use high forces to open up blocked arteries, fluid pressures used to actuate the balloon can be very high (more than 20 atmosphere). With a compliant balloon material, this requires very thick elastomeric materials to be used. Thick compliant materials can withstand such high pressures, and adequately retract into their original dimension to allow for retraction through the lumen, however their thickness is counter to the desire of having non-expanded small dimensions. Non-compliant balloon materials can be constructed having thinner balloon wall dimensions, but a downside of using non-compliant balloon materials is that they have to be folded to reduce their non-expanded size.

Moreover, both compliant as well as non-compliant balloon materials have to be pneumatically actuated, therefore one has to provide a fluid access lumen through the complete catheter system. The walls of such an access lumen have to be sufficiently strong to withstand the pressure, but this design demand is in contrast to using highly flexible, thin catheter systems.

A further downside of using a pneumatic actuation principle for expanding the balloons is the risk of having leaks in the balloon. These can originate during expansion in calcified lesions. As the creation of leaks will prevent further expansion, this can lead to very serious situations, for example, with a balloon expanded stent procedure, this can lead to a partially-deployed, and thus unstable, stent. As a result, the catheter is often of a thick and bulky shaft-like construction. For most applications, small diameters and high flexibility are of great importance. For example, with neurological procedures, or procedures within the lower extremities having mostly torturous vessels, such fluid-driven elastomeric catheters and their relatively large diameters, are simply unusable. Further complicating matters is the fact that such balloon constructions can only be made to a certain minimum diameter, thus preventing usage in such lumens, as well as lumens which have been reduced to a small diameter due to a condition requiring the angioplasty. Especially challenging is the use of current balloon catheters when stenting a bifurcation. This requires two balloons to be used in parallel, doubling the space requirements.

SUMMARY OF THE DISCLOSURE

In accordance with one aspect of the disclosure, a radially expanding nanopaper actuation system catheter is disclosed which may include an electrode, a membrane surrounding the electrode, a ring of nanotube paper (bucky paper) surrounding the membrane, electrically conductive fluid injected into the nanotube paper, and an elastic sheath mounted about the electrode, nanotube paper, and electrically conductive fluid.

In accordance with another aspect of the disclosure, a method of radially expanding the distal section of an angioplasty catheter is disclosed which may comprise navigating a distal end of the catheter to a procedure site, wherein the distal end includes a construction having a nanotube paper ring acting as one electrode surrounding a membrane surrounding a second electrode, and energizing the electrode pair. The distal end of the catheter further includes an electrolyte fluid within the nanotube paper, and an elastic sheath surrounding the nanotube paper. The energization of the electrode generates microbubbles in the nanotube paper thereby causing the nanotube paper to expand. This catheter system is also referred to in the following text as a "balloon" catheter.

In accordance with another aspect of the disclosure, a "balloon" catheter is disclosed which may comprise a conduit having a distal end and a proximal end, and means for expansion disposed in the distal end of the conduit, which means are electrically actuated.

In accordance with yet another aspect of the disclosure, a medical device is disclosed which may comprise a substantially rigid tube having a closed end and an open end, nanotube paper disposed in the substantially rigid tube at the closed end, electrically conductive fluid dispersed in the nanotube paper, an electrode coupled to the nanotube paper and electrically conductive fluid, and a second electrode separated from the nanotube paper by a membrane, and a deployable member disposed in the substantially rigid tube proximate the open end.

These and other aspects and features of the disclosure will become more apparent upon reading the following detailed description when taken into consideration with the accompanying drawings.

BRIEF DESCRIPTION OF THE DRAWINGS

FIG. 1 is a schematic representation of a system constructed in accordance with the teachings of the disclosure;

FIG. 2 is a sectional view of the balloon assembly of FIG. 1 taken along the line of 2—2 of FIG. 1;

FIG. 3 is a sectional view of the balloon assembly of FIG. 2, but depicted in an expanded or actuated state;

Figure 4:
FIG. 4 is a longitudinal sectional view through the nanotube paper of FIG. 1 taken along the line 4—4 of FIG. 1.

While the disclosure is susceptible to various modifications and alternative constructions, certain illustrative embodiments thereof have been shown in the drawings and will be described below in detail. It should be understood, however, that there is no intention to limit the disclosure to the specific forms disclosed, but on the contrary, the intention is to cover all modifications, alternative constructions, and the equivalents falling within the spirit and scope of the invention as defined by the appended claims.

DETAILED DESCRIPTION

Referring now to the drawings, and with specific reference to FIG. 1, a medical device or system constructed in accordance with the teachings of the disclosure is generally referred to by reference numeral 20. While the following disclosure will be made with primary reference to a catheter, specifically an angioplasty catheter, it is to be understood that the teachings of the disclosure can be used in conjunction with many other types of medical devices wherein the expansion of the device through the use of electrical energization, such as but not limited to, deploying stents, releasing medication or other pharmaceuticals, movement of a guide wire or the like, are certainly encompassed by the present disclosure.

The system 20, as depicted in FIG. 1, may include a catheter 22 having a distal end 24 and a proximal end 26. While not depicted, it is to be understood that the proximal end 26 would be the end manipulated by a physician or the like and that the distal end 24 would be the end navigated through a lumen or other passageway of the human body for the performance of various medical procedures. At the distal end 24, a balloon assembly 28 may be provided. As shown in FIG. 1, as well as the sectional views of FIGS. 2 and 3, the balloon assembly 28 may include a central core or electrode 30 about which is provided a proton exchange membrane 31, which itself is surrounded by a tube of nanopaper 32. Around the tube of nanopaper 32, an elastomeric membrane 34 may be provided. A function of the electrically isolating, porous membrane is to allow protons and electrons to pass through the fluid entrained in its porous structure, thereby closing the electric circuit between the two electrodes.

Figure 5:
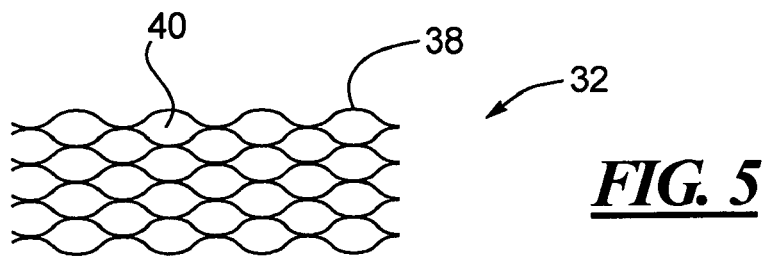
FIG. 5 is a longitudinal sectional view similar to FIG. 5, but depicted in an expanded state.

Referring now to FIGS. 4 and 5, the nanotube paper 32 is shown in detail to include a plurality of layers 38 between which are provided a plurality of voids 40. Each of the layers 38 may be substantially corrugated in shape and positioned so as to form the voids 40 depicted in FIG. 5, or can be alternatively formed as by angular shapes or the like in the voids 40. Within the voids 40, an electrically conductive solution is placed, as by injection or the like, the importance of which will be described in further detail herein.

Referring again to FIG. 1, it will be noted that the system 20 further includes first and second conductors or wires 42 and 44 which extend from a power source 46 through the catheter 22 to the balloon assembly 28. More specifically, at the balloon assembly 28, the wire 42 is connected to the electrode 30, whereas the wire 44 is connected to the connector ring 36. The connector ring 36 is further connected to the nanotube paper 32 and thereby to the electrolyte 31. A proton exchange membrane 48 may be provided about the electrode as depicted in FIGS. 2 and 3.

With respect to materials, a variety of combinations can be employed, with an exemplary embodiment including an electrode 30 manufactured from gold or platinum. While other electrical conductors can certainly be employed, the use of gold or platinum further provides the feature of radiopacity to thus facilitate visibility of the device during fluoroscopy or the like. With regard to the outer sheath 34, it can be manufactured from any elastomeric material including, but not limited to, latex, silicon rubber, and Pebax®, although many other elastic materials can certainly be employed. The electrolyte 31 can also be provided in a variety of forms, although the inventors have found the use of sodium chloride or hydrogen chloride to be particularly effective. The use of sodium chloride is beneficial in that sodium chloride is naturally present within human blood, thus making any potential leaks less problematic.

Turning to the nanotube paper 32, any form of commercially available carbon nanotube paper could be employed. It could be provided, for example, in the form of that disclosed in an article entitled *Actuator Response from Carbon Nanotube Sheets*, authored by G. M. Spinks, et al., the disclosure which is expressly incorporated herein by reference. Another reference to produce this so-called "bucky" paper is described in "*Large scale purification of single-wall carbon nanotubes: process, product and characterization*", authored by A. G. Rinzler, J. Liu et al., Applied physics A A67, 29–37 (1998). Specifically, as depicted in FIGS. 4 and 5, the nanotube paper may include single walled carton nanotubes suspensions that are vacuum-filtered to produce freestanding highly entangled nanotube ropes 50. Such single walled nanotubes are commercially available as an aqueous suspension from, for example, Rice University of Houston, Tex. Nanotube mats are typically made by vacuum filtration through a poly (tetrafluoro ethylene) filter of approximately 4 grams of a 0.6 milligram-per-milliliter nanotube suspension further diluted by the addition of approximately 80 milliliters of deionized water. The nanotube mat is then washed by 2×100 milliliters deionized water and 1×100 methanol followed by drying and vacuum at 70° Celsius for twelve hours. The typical nanotube mat produced is between 15 to 35 microns thick and has a bulk density of 0.3 to 0.4 grams per cubic centimeter and a four point conductivity of 5,000 S/cm. The nanotubes spontaneously aggregate into bundles or ropes of approximately 10 nanometers in diameter and many microns in length. The nanotube mats are then peeled from the filter to produce freestanding films for use.

In operation, the system 20 can be employed for medical procedures such as but not limited to angioplasty wherein the catheter 22 is navigated through a lumen (not shown) until the distal end 24 is appropriately positioned, such as within a blocked area of an artery. Once so positioned, the power source 26 can be actuated so as to direct a voltage, such as 1.2 volts, through the conductors 42 and 44. The resulting current flow results in microbubbles 52 being formed within the fluid 41 contained with the voids 40. Gas ($Cl_2$ and/or $O_2$) formation at the electrode surface starts due to the following two reactions

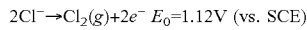

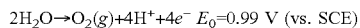

As a result of gas being trapped within the pores of the carbon nanotube mat, the thickness of the carbon nanotube mat increases. As shown best in FIGS. 3 and 5, such creation of microbubbles causes the volume of the fluid 31 to greatly expand, which in turn causes the ropes 50 forming the nanotube paper 32 to move apart. Using a nanotube paper 32, such as that disclosed above, such actuation can cause nanotube paper 32 to increase in thickness by up to 300%, with the length β of the nanotube paper 32 remaining substantially the same. The expansion of the nanotube paper 32 in turn causes the elastic sheath 34 to radially expand as well, which in turn imparts force against the interior surface of the lumen, clearing the blockage. As the micro gas bubbles are trapped within the nanotube paper, there is no essential need for an enclosed system. One could therefore use sodium chloride as the electrolyte given its pre-existing presence in the blood.

Once the balloon assembly 28 is fully expanded to clear the blockage, the power source 46 can be deenergized. The microbubbles 42 will therefore no longer be generated, and the existing microbubbles 42 will reoxidize electrochemically, thereby reversing the potential supported by the radially inward acting force from the outer elastic sheath 34. Removal of the microbubbles 42 enables the sheath 34, which is elastic, to reconstrict, and thereby recompress the nanotube paper 32 back to its original diameter. Once back to its original diameter, the balloon assembly 28 and catheter 22 can be successfully withdrawn from the lumen, or reactivated.

Figure 6:
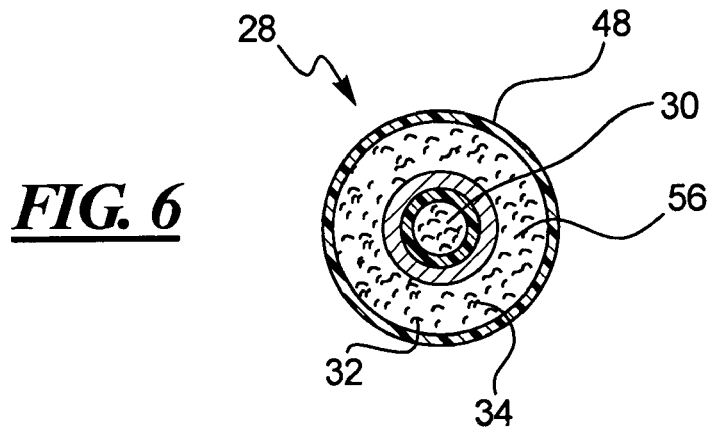
FIG. 6 is a sectional view of an alternative embodiment of a balloon assembly constructed in accordance with the teachings of the disclosure.

Referring now to FIG. 6, an alternative embodiment of the balloon assembly 28 is shown in cross-section. As shown therein the balloon assembly is substantially the same as that depicted in the first embodiment. Wherein like elements are employed, like reference numerals are used. However, such an embodiment further includes a plurality of radial slits 56 through the nanotube paper 32. As indicated above, during expansion, the nanotube paper 32 can expand in circumference by up to 300%. The resulting tangential stress on the paper can lead to radial cracks detrimentally affecting the performance of the balloon assembly 28. Accordingly, the radial cuts 56 may be made along the longitudinal axis of the nanotube paper 32 prior to mounting the sheath 34.

Figure 7:
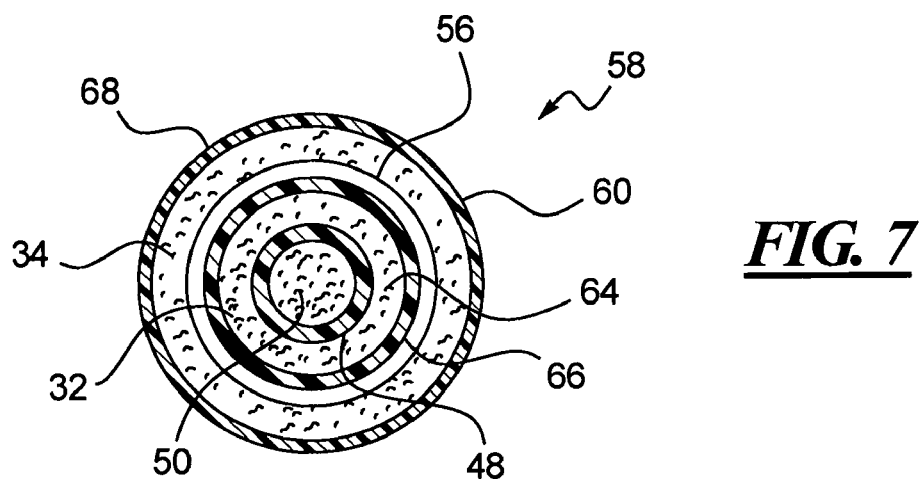
FIG. 7 is a sectional view through a second alternative embodiment of a balloon assembly constructed in accordance with the teachings of the disclosure.

As indicated above, in one exemplary embodiment, the nanotube paper 32 employed has a thickness of between 15 and 35 micrometers. However, the scope of the disclosure certainly includes other dimensions, with such thicknesses being advantageous depending upon the size of the lumen through which the catheter 22 is to be navigated. One way to change the resulting diameter would be to use a multi-layered construction as depicted in FIG. 7. As shown therein, the balloon assembly 58 includes a second ring 60 of nanotube paper 62. In addition, to serve as an electrical connection, a metallic coating 64 could be provided around an outer surface 66 of the first ring of nanotube paper 32 with the elastic sheath 34 being provided around an outer surface 68 of the second ring 60. In addition, it should be noted that in the depicted embodiment, a plurality of slits 56 is provided through each of the first and second rings 32, 60. It is to be understood that such a multi-ringed embodiment could be produced without slits as well.

In addition, while not depicted, it will be understood that separate electric connections can be provided to both the electrode 30 and metallic coating 64 to separately and selectively actuate each of the rings 32 and 60. Accordingly, depending upon the ring being actuated, the thickness or diameter of the resulting balloon assembly 58 can be tailored to the specific lumen diameter.

Figure 8:
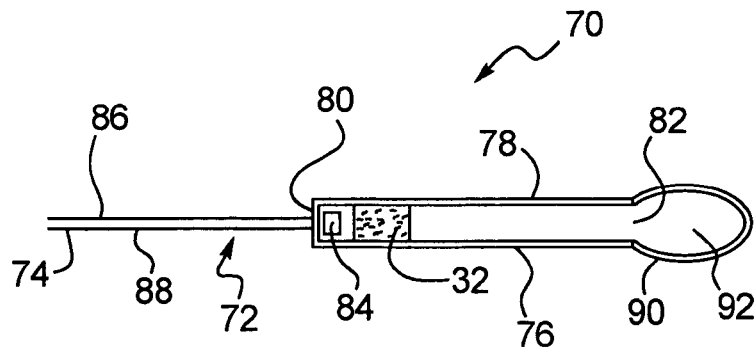
FIG. 8 is a schematic representation of an alternative system constructed in accordance with the teachings of the disclosure and employing a substantially rigid tube.
Figure 9:
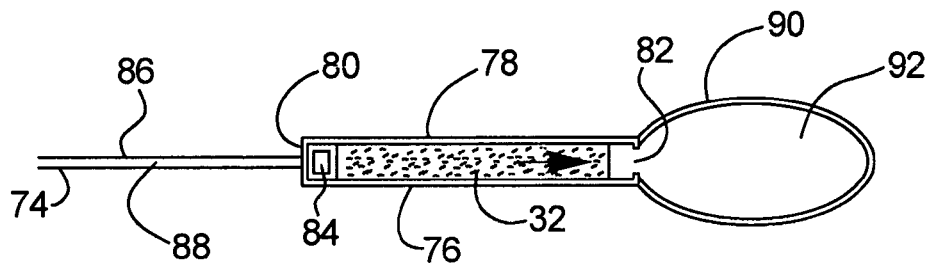
FIG. 9 is a schematic representation similar to that of FIG. 8 but depicting the system in a deployed state.

In a still further embodiment, depicted in FIGS. 8 and 9, the nanotube paper 32 can be used to expand in a longitudinal direction, as opposed to the radial expansion depicted in the first three embodiments. More specifically, a medical device 70 is depicted in FIGS. 8 and 9 and can be placed at, for example, a distal end 72 of a guide wire 74 or the like. The medical device 70 may include a substantially rigid tube 76 manufactured of a suitable polymer, metal, or ceramic and may include a cylindrical sidewall 78, a closed end 80, and an open end 82. An electrode 84 may be provided proximate the closed end 80 and be electrically connected to conductors 86, 88. The nanotube paper 32 is placed within the substantially rigid tube 76 proximate the electrode 84. A deployable member 90 may then be placed next to the nanotube paper 32 proximate the open end of the substantially rigid tube 76. In the depicted embodiment, the deployable member 90 is provided in the form of a balloon 92 filled with an electrically conductive fluid such as sodium chloride.

In still a further embodiment, multiple sections along the axial direction can be included in the "balloon" design, sharing the central electrode, but with each nanotube paper ring can be individually actuated. Such a system allows sections to be expanded in timed sequences. This for example, can be advantageous in expanding stents where either the central sections or end sections have to be expanded first. It is even possible to alternate the activation of multiple sections in order to establish a very controlled uniform radial expansion of the stent along the axial direction.

As shown in a comparison between FIGS. 8 and 9, actuation of a power source 94 energizes the electrode 84 which in turn causes the nanotube paper 32 to expand based on the principles identified above. However, since the substantially rigid tube 76 constricts radial expansion in the depicted embodiments, the nanotube paper 32 expands longitudinally as indicated by the arrow δ. Expansion of the nanotube paper 32 accordingly then causes the balloon 92 to exit through the open end 82, which, upon clearing the cylindrical sidewall 78, expands in a radial direction. Such expansion capability can be used in angioplasty procedures or the like. Since the nanotube paper 32 and balloon 92 are fixedly joined at 96, not only will the balloon 92 not exit the substantially rigid tube 76, but upon deactuation of the power source 94, the nanotube paper 32 will compress, thereby drawing the balloon 92 back into the substantially rigid tube 76.

Figure 10:
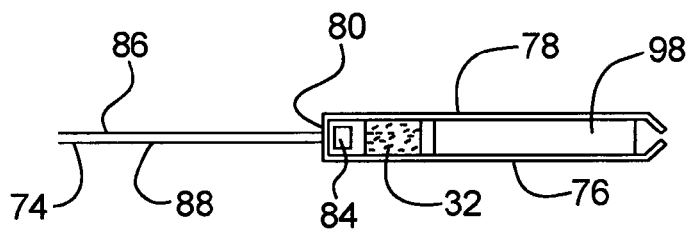
FIG. 10 is a schematic representation of a second system constructed in accordance with the teachings and of the disclosure and used for deploying medical devices or medication.
Figure 11:
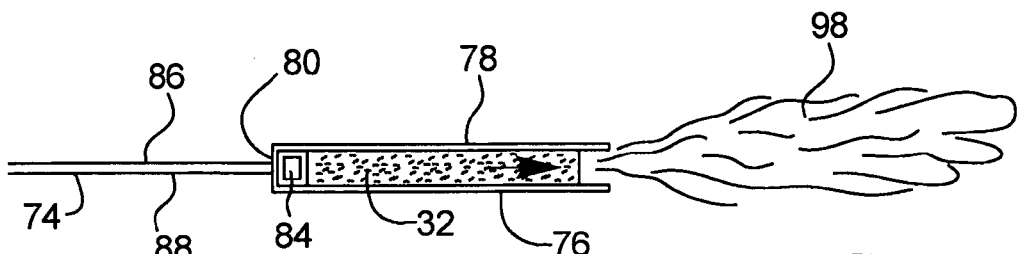
FIG. 11 is a schematic representation similar to that of FIG. 10, but depicted in a deployed state.

In a still further embodiment, depicted in FIGS. 10 and 11, the deployable member 90 can be provided in the form of another medical device or pharmaceutical 98. More specifically, as opposed to a balloon 92, FIGS. 10 and 11 indicate that a medication or pharmaceutical 98 can be provided within the substantially rigid tube 76 proximate the open end 82. In order to maintain the pharmaceutical 98 in the rigid tube until deployment is desired, a frangible membrane 100 can be provided. The frangible membrane 100 is sufficiently strong to maintain the medication or pharmaceutical 98 within the substantially rigid tube 76 under low pressure, but upon expansion of the nanotube paper 32, the resulting force of expansion as indicated by arrow δ is sufficient to overcome the frangible membrane 100, the frangible membrane 100 then ruptures, thus releasing the pharmaceutical 98. This may be particularly advantageous when releasing pharmaceuticals, such as a contrast or the like for visualization purposes of a specific area of the lumen, or protein sequences, DNA or RNA which can be injected into the vessel wall. In addition, the deployable membrane 90 could be provided in the form of a separate medical device such as a membrane wire or gel for use in treating an aneurysm or the like.

From the foregoing, one of ordinary skill in the art will appreciate that the teachings of the disclosure can be used to construct an electrically actuated medical device for use in enlarging lumens or deploying other medical devices within lumens of the body. In comparison to pneumatic actuated balloon catheters, it will be clear that there is no need for fluid access lumens.

What is claimed is:

1. A medical device, comprising:
   an electrode;
   a ring of nanotube paper surrounding the electrode;
   an electrolyte injected into the nanotube paper; and a balloon membrane surrounding the nanotube paper;
   two conductors attached respectively to the electrode and the nanotube paper.

2. The medical device of claim 1, wherein the electrolyte is an aqueous electrolyte.

3. The medical device of claim 1, wherein the electrolyte is aqueous sodium chloride.

4. The medical device of claim 1, wherein the device compromises a catheter.

5. The medical device of claim 4, wherein the catheter extends longitudinally from the nanotube paper at a distal end of the catheter to a user engageable proximal end.

6. The medical device of claim 1, further comprising an inner membrane surrounding the electrode and disposed between the electrode and the nanotube paper.

7. The medical device of claim 6, wherein the inner membrane is a proton exchange.

8. The medical device of claim 1, wherein the ballon membrane is made of a polymer.

* * * * *